US011259685B2

(12) United States Patent
Xie et al.

(10) Patent No.: US 11,259,685 B2
(45) Date of Patent: Mar. 1, 2022

(54) ENDOSCOPIC OCT PROBES WITH IMMERSED MEMS MIRRORS

(71) Applicant: UNIVERSITY OF FLORIDA RESEARCH FOUNDATION, INCORPORATED, Gainesville, FL (US)

(72) Inventors: Huikai Xie, Gainesville, FL (US); Sanjeev Jagannatha Koppal, Gainesville, FL (US); Xiaoyang Zhang, Alviso, CA (US); Liang Zhou, Gainesville, FL (US); Can Duan, Dallas, TX (US)

(73) Assignee: THE UNIVERSITY OF FLORIDA RESEARCH FOUNDATION, INCORPORATED, Gainesville, FL (US)

( * ) Notice: Subject to any disclaimer, the term of this patent is extended or adjusted under 35 U.S.C. 154(b) by 305 days.

(21) Appl. No.: 16/316,694

(22) PCT Filed: Jul. 28, 2017

(86) PCT No.: PCT/US2017/044401
§ 371 (c)(1),
(2) Date: Jan. 10, 2019

(87) PCT Pub. No.: WO2018/023010
PCT Pub. Date: Feb. 1, 2018

(65) Prior Publication Data
US 2019/0150715 A1    May 23, 2019

Related U.S. Application Data

(60) Provisional application No. 62/368,582, filed on Jul. 29, 2016.

(51) Int. Cl.
*A61B 1/00* (2006.01)
*A61B 1/05* (2006.01)
*A61B 1/06* (2006.01)
*A61B 1/07* (2006.01)
*A61B 5/00* (2006.01)
*A61B 1/04* (2006.01)

(52) U.S. Cl.
CPC ............ *A61B 1/00* (2013.01); *A61B 1/00096* (2013.01); *A61B 1/00165* (2013.01);
(Continued)

(58) Field of Classification Search
None
See application file for complete search history.

(56) References Cited

U.S. PATENT DOCUMENTS

| 8,060,187 | B2 | 11/2011 | Marshik-Geurts et al. |
| 2010/0157308 | A1 | 6/2010 | Xie |
| 2011/0137178 | A1 | 6/2011 | Tierney et al. |
| 2012/0330157 | A1* | 12/2012 | Mandella ............ G02B 26/101 600/443 |

FOREIGN PATENT DOCUMENTS

| JP | 2013-507189 A | 3/2013 |
| WO | WO 2009/137704 A1 | 11/2009 |
| WO | WO 2014/157645 A1 | 10/2014 |
| WO | WO-2014157645 A1 * | 10/2014 ........... G02B 27/283 |

OTHER PUBLICATIONS

Jia, et al., "An Electrothermal Tip-Tilt-Piston Micromirror Based on Folded Dual S-Shaped Bimorphs," J. Microelectromechanical Syst., Oct. 2009, vol. 18, No. 5, pp. 1004-1015, IEEE, USA.
(Continued)

*Primary Examiner* — Darryl J Collins
*Assistant Examiner* — Tamara Y. Washington
(74) *Attorney, Agent, or Firm* — Alston & Bird LLP

(57) ABSTRACT

Methods and apparatuses for enlarging the optical scan angle of imaging probes are provided. The optical scan angle of endoscopic probes can be increased by employing the
(Continued)

"Snell's Window" effect. An endoscopic probe can include an endoscope shell, a device for capturing electromagnetic radiation, and a liquid or gel provided between the device for capturing electromagnetic radiation and the endoscope shell. The endoscope probe can further include a first mirror placed such that electromagnetic radiation entering through the endoscope shell can bounce off the first mirror and enter the device for capturing electromagnetic radiation. The first mirror can be a microelectromechanical systems (MEMS) mirror.

29 Claims, 7 Drawing Sheets

(52) U.S. Cl.
CPC ...... *A61B 1/00172* (2013.01); *A61B 1/00177* (2013.01); *A61B 1/042* (2013.01); *A61B 1/05* (2013.01); *A61B 1/0638* (2013.01); *A61B 1/0684* (2013.01); *A61B 1/07* (2013.01); *A61B 5/0066* (2013.01); *A61B 1/00183* (2013.01); *A61B 2505/05* (2013.01); *A61B 2562/028* (2013.01); *A61B 2562/0233* (2013.01); *A61B 2562/168* (2013.01)

(56) References Cited

OTHER PUBLICATIONS

Huang, David, et al., "Optical Coherence Tomography," Author Manuscript, HHS Public Access, retrieved from <https://www.ncbi.nlm.nih.gov/pmc/articles/PMC4638169/pdf/nihms692532.pdf> on Dec. 12, 2018, Published in final edited form as: Science. Nov. 22, 1991; 254(5035): 1178-1181.

International Searching Authority, International Search Report for International Application No. PCT/US2017/044401, dated Sep. 22, 2017, 4 pages, Korean Intellectual Property Office, Korea.

Sun, Jingjing, et al., "3D In Vivo optical coherence tomography based on a low-voltage, large-scan-range 2D MEMS mirror", OPT. Express, 2010, vol. 18, No. 12, pp. 12065-12075, retrieved from <https://www.osapublishing.org/oe/fulltext.cfm?uri=oe-18-12-12065&id=199707> on Dec. 12, 2018.

Zhang, Xiaoyang, et al., "Wide-angle structured light with a scanning MEMS mirror in liquid", OPT. Express, 2016, vol. 24, No. 4, 10 pages, retrieved from <https://www.researchgate.net/publication/294105854_Wide-angle_structured_light_with_a_scanning_MEMS_mirror_in_liquid> on Dec. 12, 2018.

\* cited by examiner

ENDOSCOPIC OCT PROBES WITH IMMERSED MEMS MIRRORS

STATEMENT OF GOVERNMENT SUPPORT

This invention was made with government support under grant number 1514154 and 1512531 awarded by the National Science Foundation. The government has certain rights in the invention.

CROSS REFERENCE TO RELATED APPLICATIONS

This application is a National Stage Application, filed under 35 U.S.C. § 371, of International Application No. PCT/US2017/044401, filed Jul. 28, 2017, which claims the benefit of U.S. Provisional Patent Application Ser. No. 62/368,582, filed Jul. 29, 2016, which is incorporated herein by reference in its entirety, including any figures, tables, and drawings.

BACKGROUND OF THE INVENTION

Optical coherence tomography (OCT) is an established biomedical imaging technique which is able to obtain in vivo, real-time cross-sectional information of biological tissues with high resolution. Electrothermal microelectromechanical systems (MEMS) mirrors have been extensively used in endoscopic OCT imaging probes due to their small size, large linear range, low voltage and high fill factor. As one featured application, endoscopic OCT can be employed for internal organ imaging to aid in early stage cancer detection. Although OCT has proven to be a useful tool, one of the major challenges is assembling optical scan components into an endoscopic imaging probe that is less than a few millimeters in size. In addition, due to the relatively small mechanical rotation angle of MEMS mirrors as well as the size constraints of endoscopic imaging probes, the optical scan angle is limited. Therefore, there is always a need for methods and apparatuses to enhance the optical scan angle of imaging probes while still maintaining their compact size.

BRIEF SUMMARY

Embodiments of the present invention include methods and apparatuses for enlarging the optical scan angle of imaging probes. Embodiments of the present invention can increase the optical scan angle of imaging probes with electrothermal MEMS mirrors by employing the "Snell's Window" effect and reduce the number of insertions required for an imaging probe to completely capture the full-circumferential image of a tubular organ like an esophagus or a bronchia. Embodiments of the present invention include an MEMS OCT imaging probe that can produce a full scan of a lumen in one insertion. In addition, by immersing an MEMS mirrors in liquid, shock resistance can also be increased.

According to embodiments of the present invention, the field of view (FOV) of an endoscope probe can be increased by utilizing a liquid within an endoscopic shell. The scan range can be enlarged by harnessing the advantages of Snell's window effect. Embodiments of the present invention can be used in OCT imaging systems.

According to an embodiment of the present invention, an endoscopic probe can include an endoscope shell, a means for capturing electromagnetic radiation, and a liquid or gel provided between the means for capturing electromagnetic radiation and the endoscope shell. The liquid or gel may completely or partially immerse the means for capturing electromagnetic radiation. The endoscopic probe can further include a first mirror placed such that electromagnetic radiation entering through the endoscope shell can bounce off the first mirror and enter the means for capturing electromagnetic radiation, and the first mirror can be a microelectromechanical systems mirror. A lens can be included between the means for capturing electromagnetic radiation and the first mirror, and the lens can be a gradient-index (GRIN) lens. The means for capturing electromagnetic radiation can be a fiber (e.g., a single mode fiber (SMF)), a camera, or some other means. The endoscopic probe can be configured to be side-viewing and forward-viewing. The first mirror can tilt in one direction, two directions, and can be raised and lowered. A means for tilting or raising the first mirror can be bimorph actuator(s) and piezo electric crystal(s). For a specific example, the means for tilting or raising the first mirror can be inverted-series-connected (ISC) Al/SiO2 bimorph actuators. A second mirror can also be included that is positioned to reflect electromagnetic radiation coming from the first mirror and to the means for capturing electromagnetic radiation. In some embodiments, a prism can be used as the first mirror.

DETAILED DESCRIPTION

Figure 1:
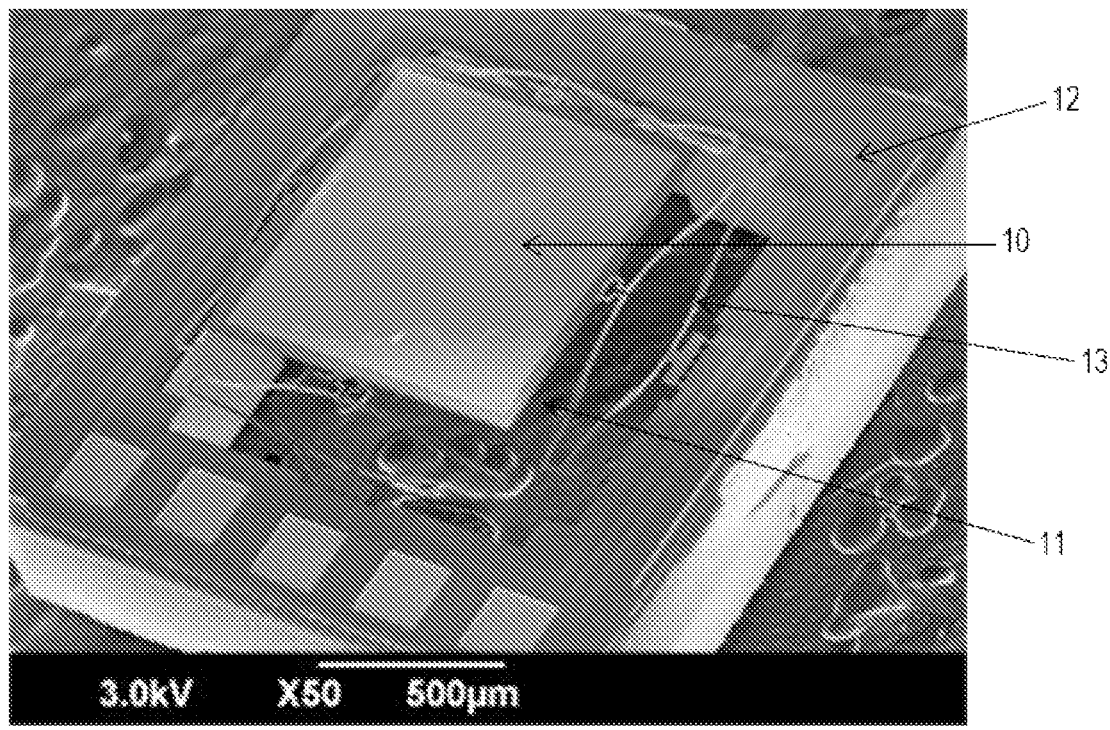
FIG. 1 is a scanning electron microscope (SEM) image of an inverted-series-connected (ISC) two-axis electrothermal MEMS mirror according to an embodiment of the present invention.

According to an embodiment of the present invention, an endoscopic probe can include an endoscope shell, a means for capturing electromagnetic radiation, and a liquid or gel provided between the means for capturing electromagnetic radiation and the endoscope shell. The endoscopic probe can further include a first mirror placed such that electromagnetic radiation entering through the endoscope shell can bounce off the first mirror and enter the means for capturing electromagnetic radiation, and the first mirror can be a microelectromechanical systems mirror. A lens can be included between the means for capturing electromagnetic radiation and the first mirror, and the lens can be a gradient-index (GRIN) lens. The means for capturing electromagnetic radiation can be a fiber (e.g., a single mode fiber (SMF)) or a camera. The endoscopic probe can be configured to be side-viewing and forward-viewing. The first mirror can tilt in one direction, two directions, and can be raised and lowered. A means for tilting or raising the first mirror can be bimorph actuator(s) and piezo electric crystal(s). In a specific example, the means for tilting or raising the first mirror is are inverted-series-connected (ISC) Al/SiO2 bimorph actuators. A second mirror can also be included that is positioned to reflect electromagnetic radiation coming from the first mirror and to the means for capturing electromagnetic radiation. The second mirror can also be configured to tilt and rise. Examples of the electromagnetic radiation that can be captured include visible light, ultraviolet (UV) light, infrared red, and near infrared light. In different embodiments, the first mirror and the second mirror can both tilt and rise, only one of the first or second mirrors can tilt or raise, or both mirrors can be fixed. The endoscope shell can be made of any materials known in the art including plastics, metals, glass, and ceramics, and the endoscopic shell can have a cross section that is oval or round. The endoscopic probe can further have a flattened optical window as well as a means of delivering electromagnetic radiation. The means for delivering electromagnetic radiation can include a fiber bundle that can both deliver and capture electromagnetic radiation. For instance, the fiber bundle can have a center fiber delivering light and surrounding fibers that capture the image, or vice versa. In some embodiments, a prism can be used as the first mirror, the second mirror, or for both the first and second mirror.

According to another embodiment of the present invention, an endoscopic probe can include an endoscopic shell, an optical window, a fiber module, and a liquid or gel provided between the optical window and the endoscope shell. The endoscopic probe can further include a first mirror placed such that electromagnetic radiation, e.g., near infrared light, entering the endoscope shell through the fiber module can bounce off the first mirror, and the first mirror can be a microelectromechanical systems (MEMS) mirror. The fiber module consists of an optical fiber and a lens, and the lens can be a gradient-index (GRIN) lens. The fiber can be a single mode fiber (SMF)). The endoscopic probe can be configured to be side-viewing and forward-viewing. The first mirror can tilt in one direction, two directions, and can be raised and lowered. A second mirror can also be included that is positioned to reflect electromagnetic radiation coming from the first mirror and to the optical window. The second mirror can also be configured to tilt and rise. Examples of the electromagnetic radiation that can be captured include visible light, ultraviolet (UV) light, infrared red, and near infrared light. In different embodiments, the first mirror and the second mirror can both tilt and rise, only one of the first or second mirrors can tilt or raise, or both mirrors can be fixed. The endoscope shell can be made of any materials known in the art including plastics, metals, glass, and ceramics, and the endoscopic shell can have a cross section that is oval or round. The endoscopic probe can further have a flattened optical window.

Electrothermal bimorph MEMS mirrors according to the present invention can have a gap 11 between the mirror plate 10 and the substrate 12, as shown by a two-axis electrothermal bimorph MEMS mirror in FIG. 1. In FIG. 1, it can be seen that the mirror plate 10 is elevated above the silicon substrate 12, leaving a gap 11 underneath the mirror plate 10. The gap 11 allows a space for liquid to fill-in and reduces the squeeze-film damping. The gap 11 also allows the mirror plate 10 to rotate in liquid without serious stiction problems, which can also be alleviated by having an appropriately sized gap.

In FIG. 1, four inverted-series-connected (ISC) Al/SiO2 bimorph actuators 13 are connected at the middle points of the four sides of the mirror plate 10 to provide out-of-plane displacement. The four actuators 13 can be separately controlled to realize tip and tilt of the mirror plate 10. Other types of actuators may also be used in the embodiments of the present invention (e.g., piezo electric actuators or electromagnetic actuators).

A liquid may be used to cover the mirror plate 10 and expand the field of view (FOV) of the mirror via the Snell's Window effect. For example, a mineral oil may be used to immerse the MEMS mirror as it is transparent and also has an effective refractive index of 1.5. Mineral oil has shown to work well in the 1,300 nm wavelength range, but other liquids can be applied and selected for their suitability depending on what wavelength range is desired to be captured. That is, instead of mineral oil, other types of liquids with varying refractive indexes can be applied in the embodiments of the present invention (e.g., water, ethylene glycol, glycerin, vegetable oils, propylene glycol, etc.). In addition, more than one liquid may be combined to form a mixture. Preferably, any liquids used would be non-toxic in case they were to leak while the device was in operation. A liquid used in the present invention can have refractive indices of, for example, any of the following values, about any of the following values, at least any of the following values, at least about any of the following values, not more than any of the following values, not more than about any of the following values, or within any range having any of the following values as endpoints (with or without "about" in front of one or both of the endpoints), though embodiments are not limited thereto: 1.05, 1.10, 1.15, 1.20, 1.25, 1.30, 1.35, 1.40, 1.45, 1.50, 1.55, 1.60, 1.65, 1.70, 1.75, 1.80, 1.85, 1.90, 1.95, and 2.00. For example, a liquid used in the present invention can have a refractive index of 1.30, about 1.30, at least 1.30, no more than 1.30, or from 1.20 to 1.40 (inclusive).

Figure 2A:
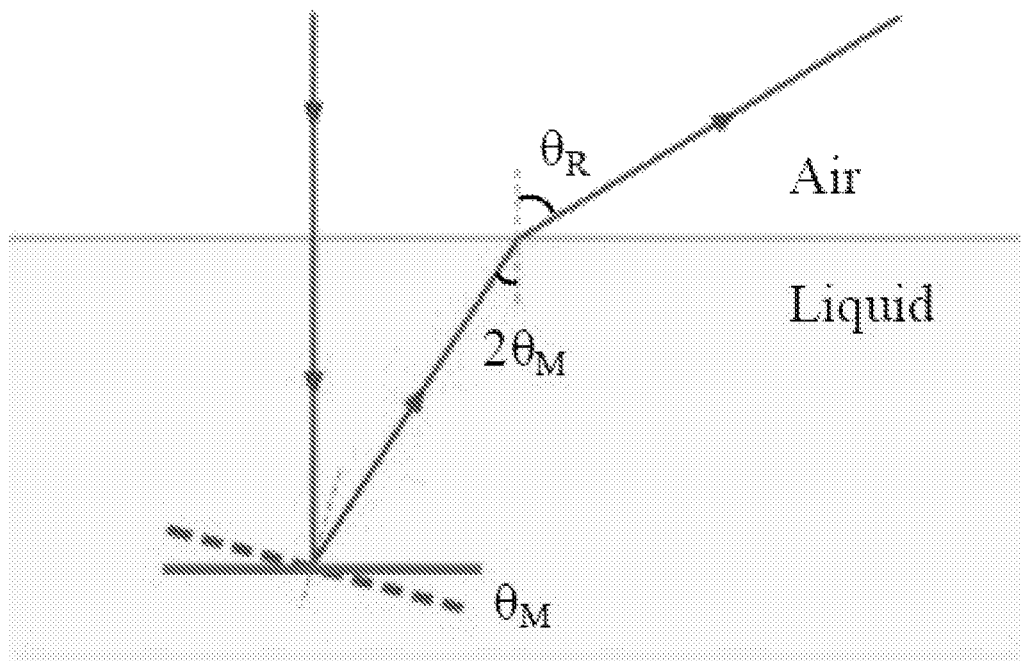
FIG. 2a and FIG. 2b show the principles of the "Snell window" effect.

A schematic diagram of the physical principles embodied in the present invention can be seen in FIG. 2a. When the mirror plate has a mechanical tilt angle $\theta M$, the output optical angle $\theta_R$ becomes $\arcsin[n \times \sin(2\theta_M)]$. When $\theta_M$ reaches the critical angle, which is 20.9° for mineral oil, $\theta_R$ becomes 90° and is more than twice as much as the optical scan angle of 41.8° in air.

Figure 2B:
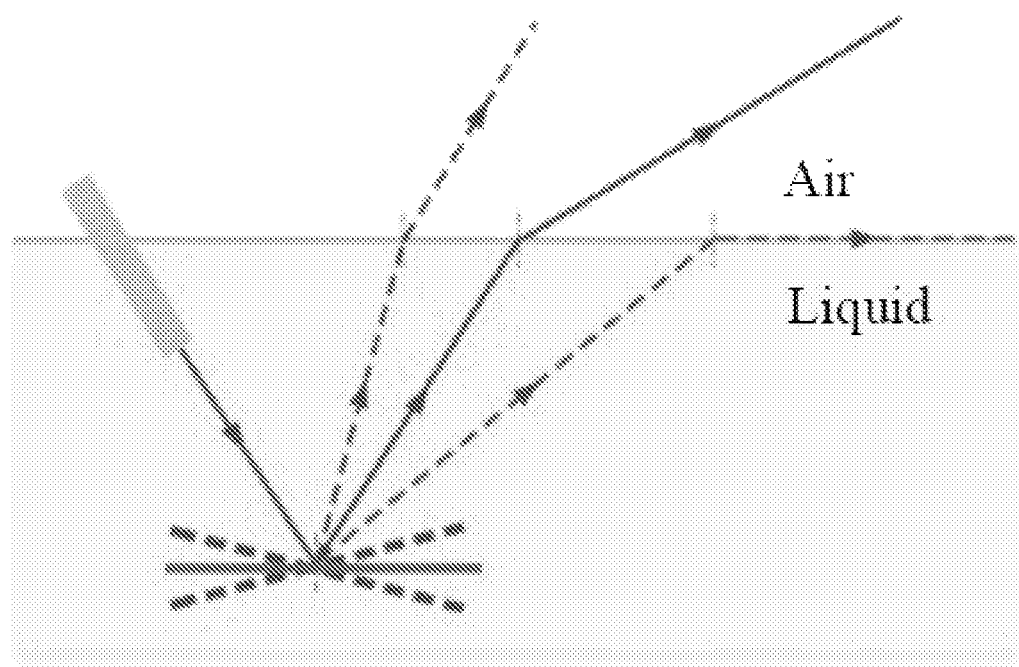

For the inverted-series-connected (ISC) MEMS mirror shown in FIG. 1, its maximum mechanical tilt angle range is ±8°. Therefore, the mirror has a total mechanical tilt of 16°, which is smaller than the critical angle. As can be seen in FIG. 2a, angle amplification increases when $\theta_M$ approaches the critical angle. Thus, in order to maximize the FOV, an oblique incidence is used. As shown in FIG. 2b, the light is incident on the mirror plate at 25.8°. In this arrangement, the output optical beam scans the liquid/air boundary from 9.8° to 41.8° when the mirror tilts from −8° to +8°. Thus, the theoretical maximum output FOV reaches 75°, which is about 2.3 times the FOV for the mirror in air.

Figure 3:
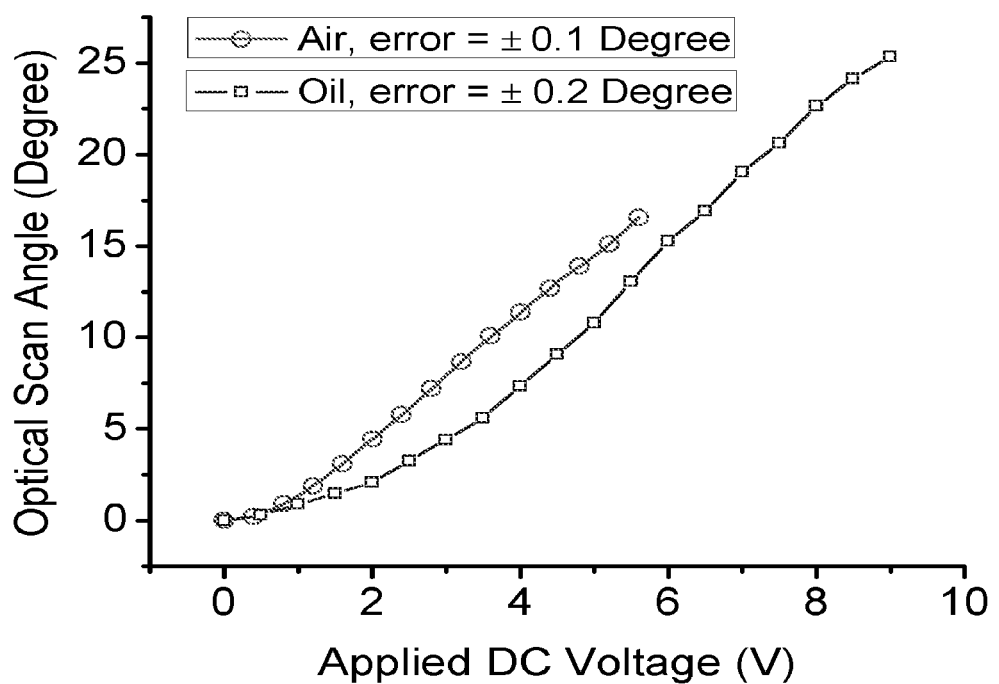
FIG. 3 is a graph showing the static response of an MEMS mirror in both air and mineral oil.

The static angular tilt angle response of an MEMS mirror in air and mineral oil is shown in FIG. 3, where only one of the four actuators was excited. The maximum optical scan angle on a single side reached 16.6° at 5.6 V in air and 25.4° at 9 V in oil. The corresponding maximum mechanical tilt angle of the mirror is 8.3° in both air and mineral oil.

Although specific tilt angles, tilting mechanisms, and voltages are given for the working prototype embodiment of FIG. 1, these figures are only examples and are not intended to limit the present invention. That is, the tilt angles, tilting mechanisms, and voltages applied can be selected depending on the application of each embodiment.

Figure 6A:
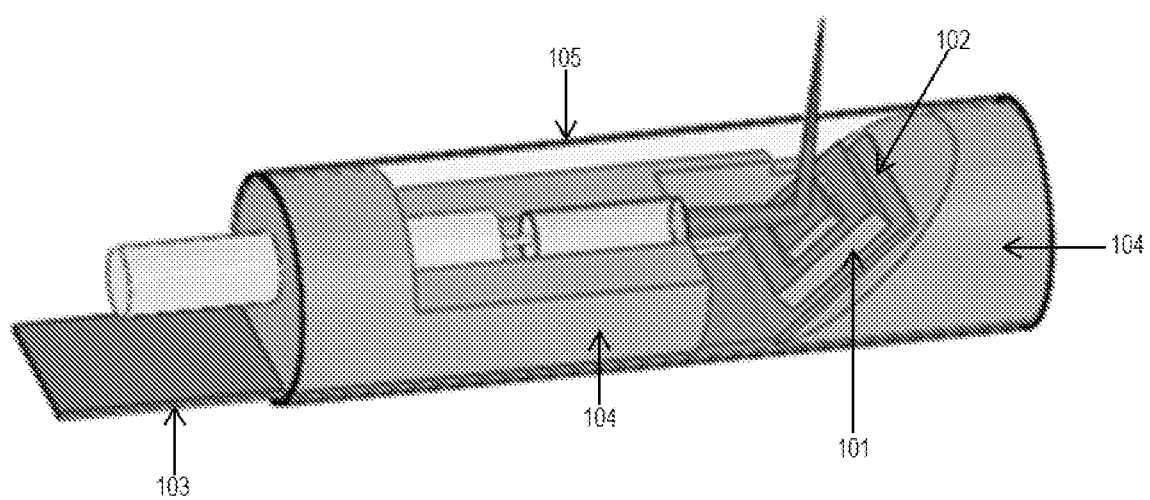
FIG. 6a and FIG. 6b show side-viewing OCT imaging probes.
Figure 6B:
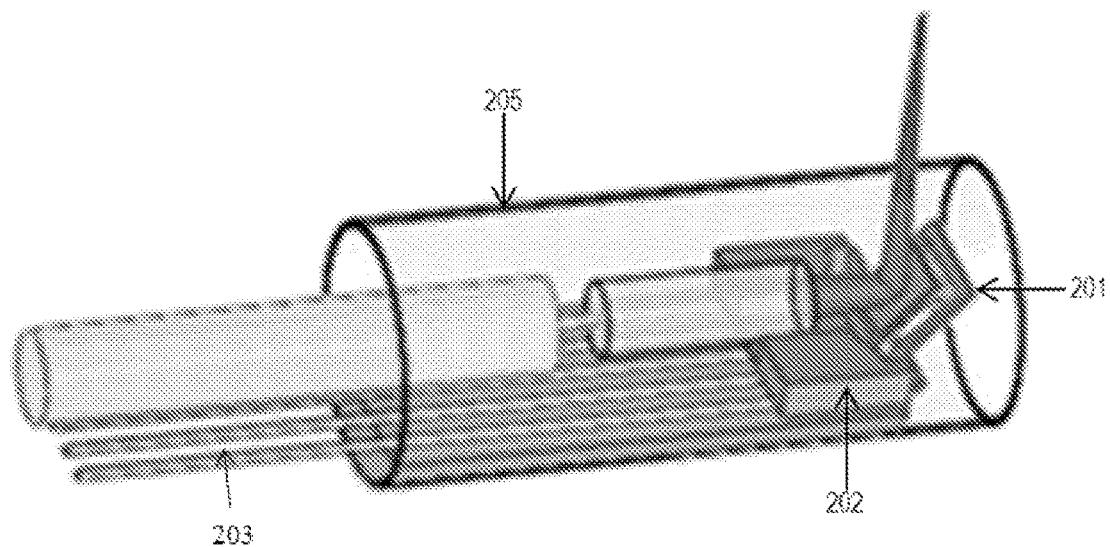

In general, there are two different types of endoscopic imaging probes, side-viewing and forward-viewing, both of which can be implemented in embodiments of the present invention. Two exemplified side-viewing probes are illustrated in FIGS. 6a and 6b. The embodiment in FIG. 6a has an MEMS mirror 101 placed on a 45° slope and is electrically connected through a flexible printed circuit board (FPCB) 102 while the embodiment in FIG. 6b has an MEMS mirror 201 with the mirror plate tilted 45° and integrated on a silicon optical bench 202. Both embodiments can have internal electrical wiring, 103 and 203, for control of the mirrors, 101 and 201, and a support framework 104 for supporting the mirrors, substrate, fiber (and/or camera), and lens (the support framework is not shown in FIG. 6b). In either the embodiment of FIG. 6a or FIG. 6b, a liquid can be filled and sealed in the endoscope shells, 105 and 205, as shown in FIG. 7.

Figure 7:
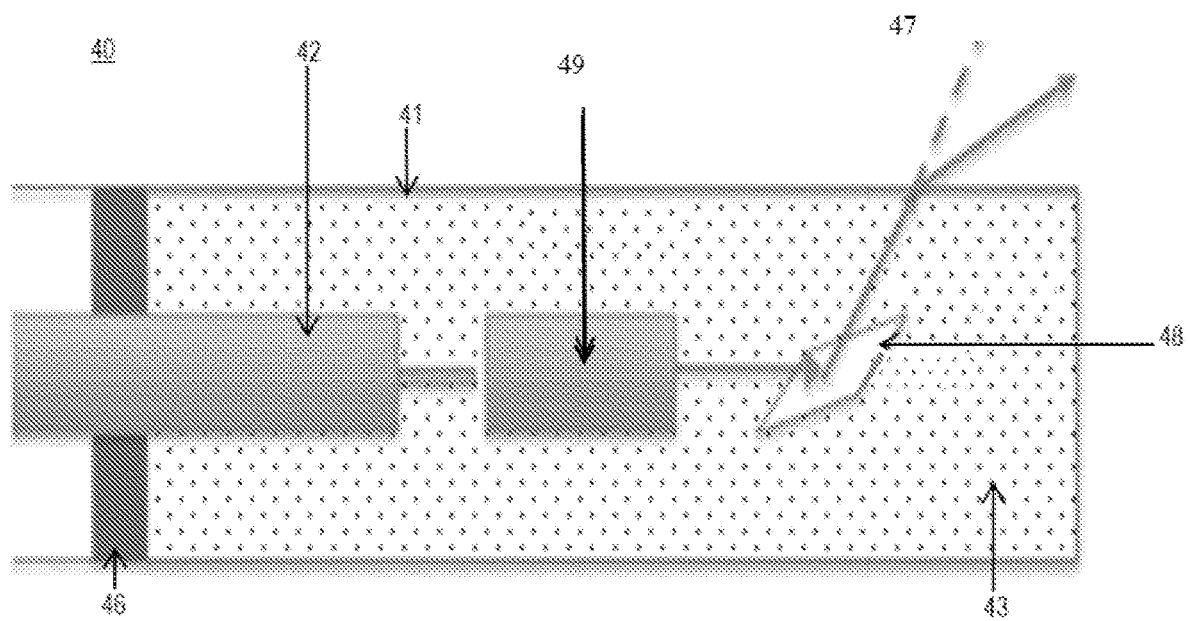
FIG. 7 is a schematic diagram of a side-viewing imaging probe according to an embodiment of the present invention.

FIG. 7 is a schematic diagram of a side-viewing imaging probe 40 (or endoscope) according to an embodiment of the present invention. FIG. 7 shows an endoscope shell 41, a lens 49 (which can be a GRIN lens), a fiber 42 or a camera to collect incoming electromagnetic radiation, a liquid 43 within the endoscope shell 41, and a seal ring 46 that forms a barrier to keep the liquid 43 in place and separated from the rest of the endoscope 40. The outside perimeter of the endoscope shell 41 can take a multitude of shapes, including but not limited to a circle, an oval, a square or a rectangle, and its edges can be smoothed. If the perimeter of the endoscope shell 41 is an oval or a circle, there can be a flattened window where light can pass through the endoscopic shell and lands on the articulating mirror 48, which may be an MEMS mirror. Examples of electromagnetic radiation that can be utilized in the embodiments of the present invention include but are not limited to ultra-violet radiation, infrared radiation, near infrared radiation and visible light.

Endoscope shells used in the present invention can have an outside diameter of, for example, any of the following values, about any of the following values, at least any of the following values, at least about any of the following values, not more than any of the following values, not more than about any of the following values, or within any range having any of the following values as endpoints (with or without "about" in front of one or both of the endpoints), though embodiments are not limited thereto (all measurements are in millimeters): 0.50, 1.0, 2.0, 3.0, 4.0, 5.0, 6.0, 7.0, 8.0, 9.0, 10.0, 11.0, 12.0, 13.0, 14.0, and 15.0. For example, an endoscope shell according to the present invention can have an outside diameter of 10.0 mm, about 10.0 mm, at least 10.0 mm, no more than 10.0, or from 8.0 mm to 10.0 mm (inclusive).

Figure 8:
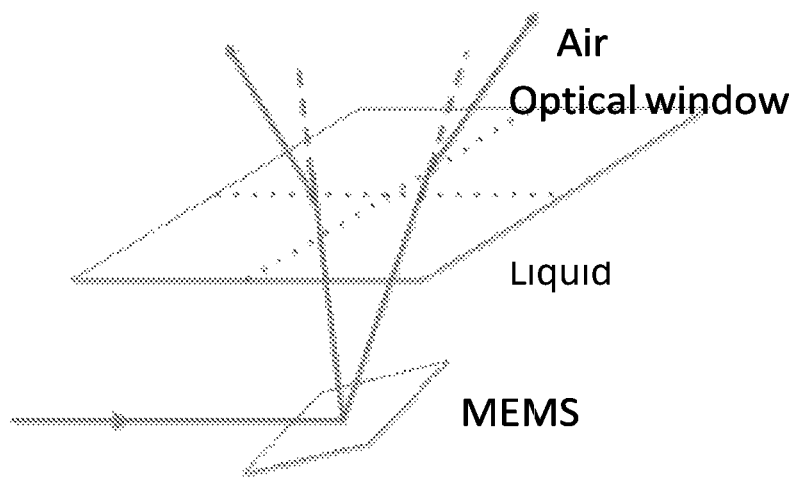
FIG. 8 illustrates basic concepts of the present invention, with an MEMS mirror directing a light beam through a liquid and toward an optical window, resulting in an amplified scan angle for both axes.

In order to improve the scan angle amplification effect, a flat optical window can be incorporated into the endoscope shell. This is especially true when the tubing is not transparent. For example, the endoscope shell can be made of circular stainless steel tubing with a glass or plastic flat viewing window. When a flat window is placed in front of a mirror plate and a liquid is filled in between the window and the mirror plate, the Snell refraction angle amplification occurs for both scan directions, as illustrated in FIG. 8.

Figure 9:
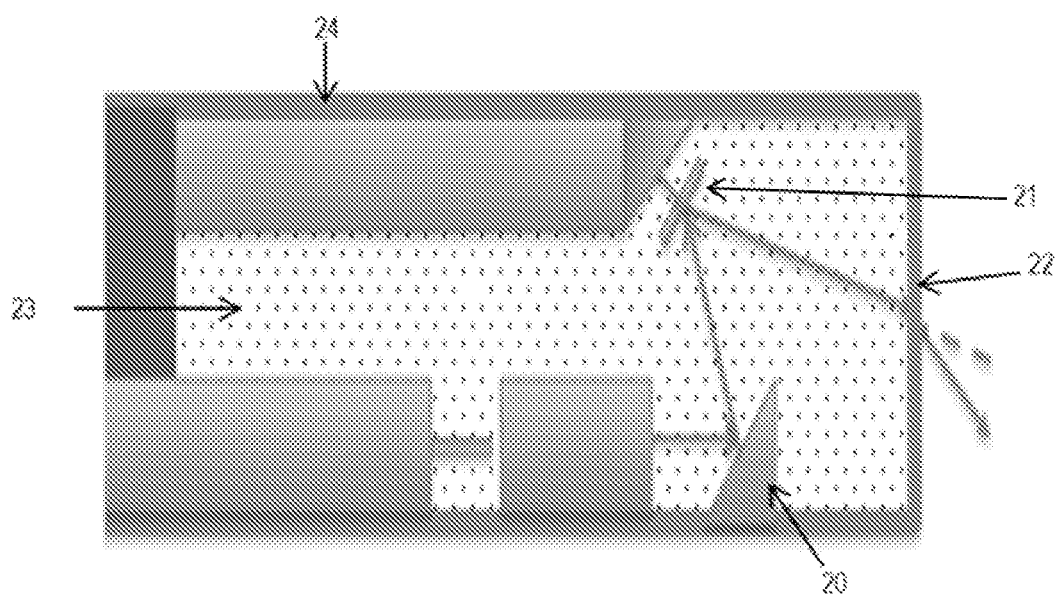
FIG. 9 is forward-viewing probe with an MEMS mirror and a fixed mirror in liquid, according to an embodiment of the present invention.

There are various forward-viewing probe designs that can be applied to the embodiments of the present invention, one of which is illustrated in FIG. 9. The incident light is reflected on a fixed mirror 20, before landing on the MEMS mirror 21, which then directs the light beam to scan forward. The endoscope shell 24 may be made of glass, metal, or metal with a glass window through which light can pass. Once the optical beam reaches the liquid/glass/air interface 22, the scan angle can be increased. This embodiment can also include a camera or a fiber to collect electromagnetic radiation bouncing off the fixed mirror 20. The embodiments of the present invention may also use the fiber or another fiber to deliver electromagnetic radiation (e.g., visible light) to the end of the endoscope.

Figure 10:
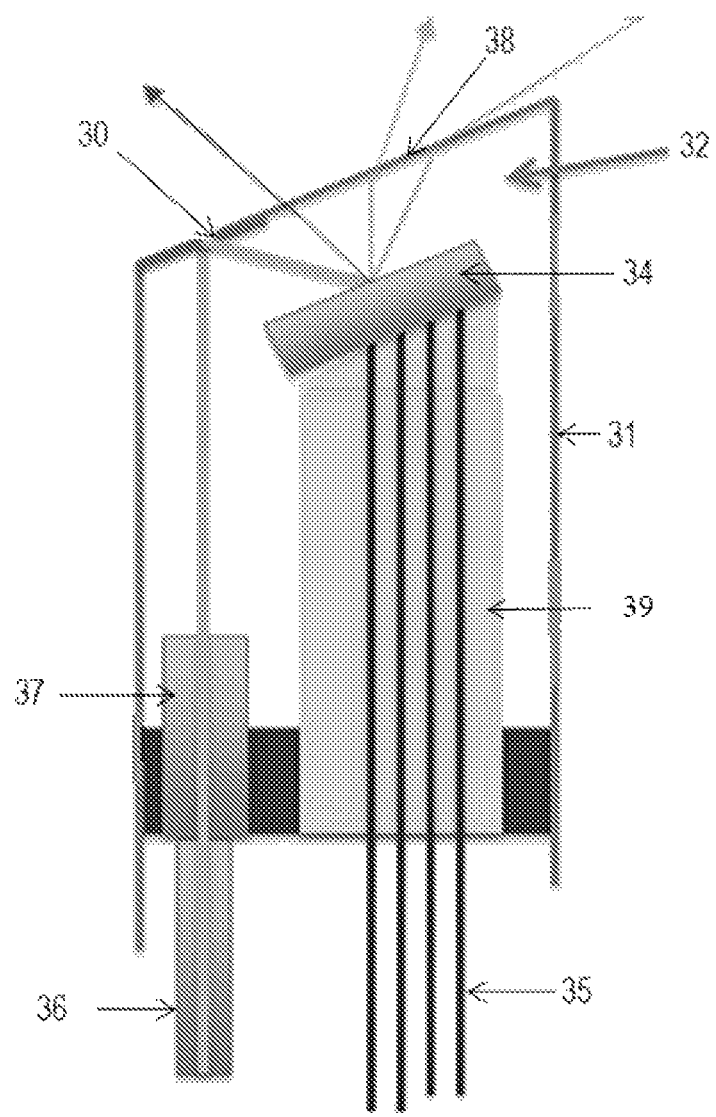
FIG. 10 is a forward-viewing probe with an MEMS mirror and a fixed mirror in liquid, according to an embodiment of the present invention.

Another design with a slightly slanted optical window is shown in FIG. 10, including a fixed mirror 30. The fixed mirror 30 can consist of a highly-reflective plate attached in front of the optical window. An endoscope shell 31 can be provided and can be made of glass, plastic, metal, or some combination of glass plastic and metal or other materials known in the art. For example, the sides of the probe may be made of metal while the tip of the probe can have a window 38, which can be made of glass or plastic. A liquid 32 can be filled inside the endoscope shell 31 and can submerse the maneuverable mirror 34 (which can be an MEMS mirror, for example). Electrical wires 35 can be run through the probe to control the movement of the maneuverable mirror 34 in all of the embodiments of the present invention, as shown in FIG. 10. A camera or a fiber 36 can be used to collect the electromagnetic radiation being reflected off of the fixed mirror 30. A lens 37 can be provided in front of or attached to the fiber 36, and the lens 37 can be a gradient-index lens. A ferule 39 may also be provided as a support structure.

A greater understanding of the present invention and of its many advantages may be had from the following example, given by way of illustration. The following example is illustrative of some of the methods, applications, embodiments and variants of the present invention. It is, of course, not to be considered as limiting the invention. Numerous changes and modifications can be made with respect to the invention.

Example 1

Figure 4:
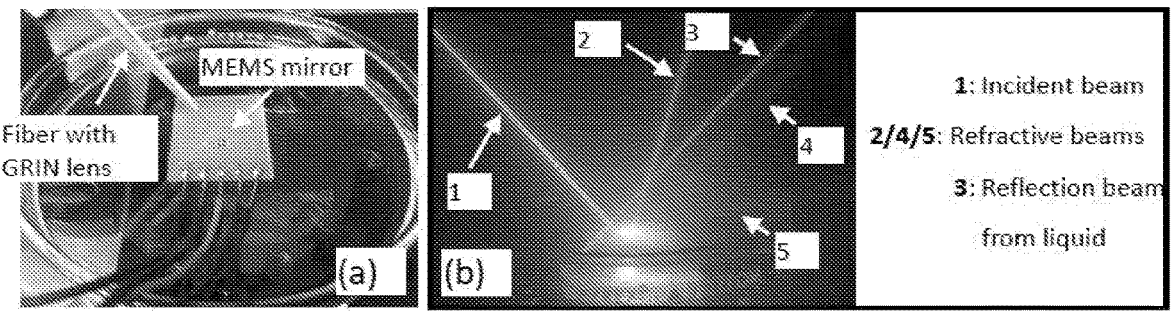
FIG. 4a shows an experimental setup of an imaging probe according to an embodiment of the present invention.
FIG. 4b is an image showing a laser used to visualize the enlarged optical scan angle in an imaging probe according to an embodiment of the present invention.

A proof of concept experiment was conducted including the fabrication of a prototype according to an embodiment of the present invention. The setup of an immersed two-axis MEMS mirror for OCT imaging experiment is shown in FIG. 4a, where a single mode fiber (SMF) with a gradient-index (GRIN) lens glued on its tip was inserted in mineral oil and pointed to a mirror with a maximum FOV angle of 25.8°, as illustrated in FIG. 2b. FIG. 4b shows a picture in which a red laser is used to visualize the enlarged optical scan angle. Note that the incident laser beam approaches the experimental setup from a medium of air. The immersed MEMS mirror was then employed in an OCT system to perform a lateral scan for imaging a piece of paper. The details of the optics for the OCT are reported in Reference [2].

Figure 5A:
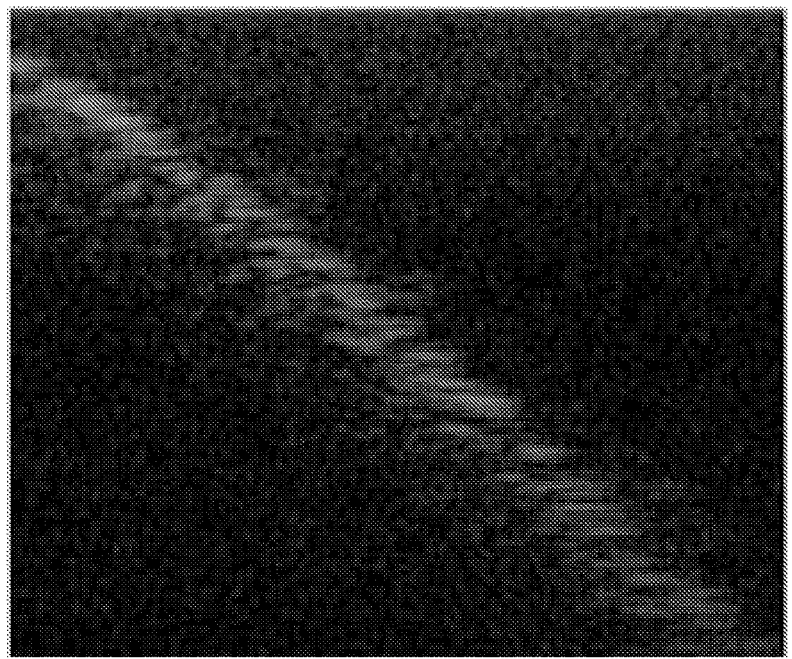
FIG. 5a is a 2D optical coherence tomography (OCT) image of a piece of paper captured using an imaging probe according to an embodiment of the present invention.
Figure 5B:
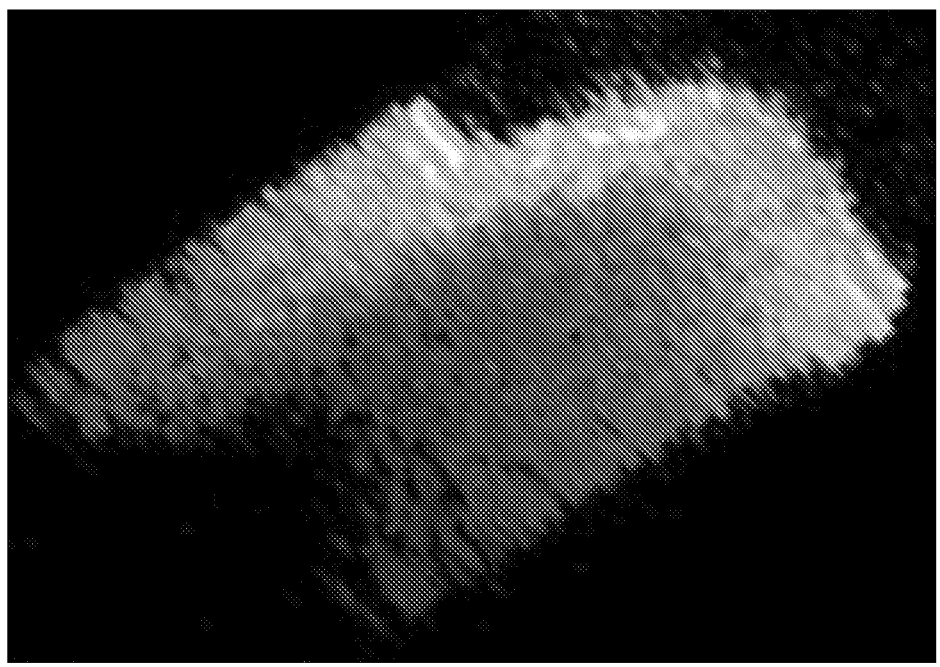
FIG. 5b is a 3D optical coherence tomography (OCT) image of a piece of paper captured using an imaging probe according to an embodiment of the present invention.

The 2D and 3D OCT images shown in FIG. 5 were acquired with two differential ramp voltages (0-8 V) applied to four actuators with the frequencies of 1.25 Hz and 450 mHz, respectively. The width of the 2D OCT image is 3.3 mm and the height is 2.5 mm. The 3D image was achieved by stacking 100 frames of 2D OCT images with dimensions of 3.3 mm by 3.3 mm by 2.5 mm. The obtained FOV was about 62°.

The subject invention includes, but is not limited to, the following exemplified embodiments.

Embodiment 1. An endoscopic probe comprising:
an endoscope shell;
a means for capturing electromagnetic radiation; and
a liquid or gel (or both) provided between the means for capturing electromagnetic radiation and the endoscope shell.

Embodiment 2. The endoscopic probe of embodiment 1, further comprising a first mirror placed such that electromagnetic radiation entering through the endoscope shell can bounce off the first mirror and enter the means for capturing electromagnetic radiation.

Embodiment 3. The endoscopic probe of embodiment 2, wherein the first mirror is a microelectromechanical systems (MEMS) mirror.

Embodiment 4. The endoscopic probe of any of embodiments 1 to 3, further comprising a lens between the means for capturing electromagnetic radiation and the first mirror.

Embodiment 5. The endoscopic probe of embodiment 4, wherein the lens is a gradient-index (GRIN) lens.

Embodiment 6. The endoscopic probe of any of embodiments 1 to 5, wherein the means for capturing electromagnetic radiation is a fiber.

Embodiment 7. The endoscopic probe of embodiment 6, wherein the fiber is a single mode fiber (SMF).

Embodiment 8. The endoscopic probe of any of embodiments 1 to 7, wherein the endoscopic probe is configured to be side-viewing.

Embodiment 9. The endoscopic probe of any of embodiments 1 to 7, wherein the endoscopic probe is configured to be forward-viewing.

Embodiment 10. The endoscopic probe of any of embodiments 2 to 9, wherein the first mirror is configured to tilt in one direction.

Embodiment 11. The endoscopic probe of any of embodiments 2 to 9, wherein the first mirror is configured to tilt in two directions.

Embodiment 12. The endoscopic probe of any of embodiments 2 to 11, wherein the first mirror can be raised and lowered.

Embodiment 13. The endoscopic probe of any of embodiments 2 to 12, wherein a means for tilting or raising the first mirror is bimorph actuator(s).

Embodiment 14. The endoscopic probe of any of embodiments 2 to 12, wherein a means for tilting or raising the first mirror is piezo electric crystal(s).

Embodiment 15. The endoscopic probe of any of embodiments 2 to 12, wherein a means for tilting or raising the first mirror is inverted-series-connected (ISC) Al/SiO2 bimorph actuator(s).

Embodiment 16. The endoscopic probe of any of embodiments 2 to 15, wherein the means for capturing electromagnetic radiation is a camera.

Embodiment 17. The endoscopic probe of any of embodiments 1 to 16, further comprising a second mirror positioned to reflect electromagnetic radiation coming from the first mirror and to the means for capturing electromagnetic radiation.

Embodiment 18. The endoscopic probe of any of embodiments 1 to 17, wherein the second mirror is configured to tilt.

Embodiment 19. The endoscopic probe of any of embodiments 1 to 18, wherein the electromagnetic radiation is visible light.

Embodiment 20. The endoscopic probe of any of embodiments 1 to 18, wherein the electromagnetic radiation is in the infrared range.

Embodiment 21. The endoscopic probe of any of embodiments 1 to 20, wherein both of the first and the second mirror are fixed.

Embodiment 22. The endoscopic probe of any of embodiments 1 to 21, wherein the endoscope shell is made of plastic, metal, or glass.

Embodiment 23. The endoscopic probe of any of embodiments 1 to 22, wherein a cross section of the endoscope shell is oval or round.

Embodiment 24. The endoscopic probe of any of embodiments 1 to 23, wherein the endoscope shell has a flattened optical window.

Embodiment 25. The endoscopic probe of any of embodiments 1 to 24, wherein the first mirror is fixed.

Embodiment 26. The endoscopic probe of any of embodiments 1 to 25, wherein the second mirror is fixed.

Embodiment 27. The endoscopic probe of any of embodiments 1 to 26, wherein the electromagnetic radiation is in the UV range.

Embodiment 28. The endoscopic probe of any of embodiments 1 to 27, further comprising a seal ring.

Embodiment 29. The endoscopic probe of any of embodiments 1 to 28, further comprising one or more optical fibers suitable for delivering electromagnetic radiation to the endoscopic probe.

Embodiment 30. The endoscopic probe of any of embodiments 1 to 29, wherein the camera has a means for tilting and raising and the means for tilting and raising can be piezoelectric and electromagnetic actuators.

Embodiment 31. The endoscopic probe of any of embodiments 1 to 30, further comprising a means for delivering electromagnetic radiation to the endoscopic shell.

Embodiment 31. The endoscopic probe of any of embodiments 1 to 30, wherein the means for delivering electromagnetic radiation to the endoscopic shell is an LED or an electromagnetic radiation transmitting fiber.

Embodiment 101. A method for capturing images using an endoscopic probe comprising:
providing a means for capturing electromagnetic radiation within an endoscope shell; and using the Snell's window effect to expand the field of view captured by the means for capturing electromagnetic radiation.

Embodiment 102. The method for capturing images using an endoscopic probe of embodiment 101, further comprising providing a mirror placed such that electromagnetic radiation entering through the endoscope shell can bounce off the mirror and enter the means for capturing electromagnetic radiation.

Embodiment 103. The method for capturing images using an endoscopic probe of any of embodiments 101 to 102, wherein the mirror is a microelectromechanical systems mirror.

Embodiment 104. The method for capturing images using an endoscopic probe of any of embodiments 101 to 103, further comprising providing a lens between the means for capturing electromagnetic radiation and the mirror.

Embodiment 105. The method for capturing images using an endoscopic probe of embodiment 104, wherein the lens is a gradient-index (GRIN) lens.

Embodiment 106. The method for capturing images using an endoscopic probe of any of embodiments 101 to 105, wherein the means for capturing electromagnetic radiation is a fiber.

Embodiment 107. The method for capturing images using an endoscopic probe of any of embodiments 101 to 106, wherein the fiber is a single mode fiber (SMF).

Embodiment 108. The method for capturing images using an endoscopic probe of any of embodiments 101 to 107, wherein the endoscopic probe is configured to be side-viewing.

Embodiment 109. The method for capturing images using an endoscopic probe of any of embodiments 101 to 107, wherein the endoscopic probe is configured to be forward-viewing.

Embodiment 110. The method for capturing images using an endoscopic probe of any of embodiments 102 to 109, wherein the mirror is configured to tilt in one direction.

Embodiment 111. The method for capturing images using an endoscopic probe of any of embodiments 102 to 109, wherein the mirror is configured to tilt in two directions.

Embodiment 112. The method for capturing images using an endoscopic probe of any of embodiments 102 to 111, wherein the mirror can be raised in lowered.

Embodiment 113. The method for capturing images using an endoscopic probe of any of embodiments 102 to 111, wherein a means for tilting or raising the mirror is bimorph actuator(s).

Embodiment 114. The method for capturing images using an endoscopic probe of any of embodiments 102 to 112, wherein a means for tilting or raising the mirror is piezo electric crystal(s).

Embodiment 115. The method for capturing images using an endoscopic probe of any of embodiments 102 to 112, wherein a means for tilting or raising the mirror is inverted-series-connected (ISC) Al/SiO2 bimorph actuator(s).

Embodiment 116. The method for capturing images using an endoscopic probe of any of embodiments 101 to 115, wherein the means for capturing electromagnetic radiation is a camera.

Embodiment 117. The method for capturing images using an endoscopic probe of any of embodiments 102 to 116, further comprising providing a second mirror positioned to reflect electromagnetic radiation coming from the first mirror and to the means for capturing electromagnetic radiation.

Embodiment 118. The method for capturing images using an endoscopic probe of any of embodiments 101 to 117, wherein the second mirror is configured to tilt using actuators or piezoelectric crystals.

Embodiment 119. The method for capturing images using an endoscopic probe of any of embodiments 101 to 118, wherein the electromagnetic radiation is visible light.

Embodiment 120. The method for capturing images using an endoscopic probe of any of embodiments 101 to 118, wherein the electromagnetic radiation is in the infrared range.

Embodiment 121. The method for capturing images using an endoscopic probe of any of embodiments 101 to 120, wherein both of the first and the second mirror are fixed.

Embodiment 122. The method for capturing images using an endoscopic probe of any of embodiments 101 to 121, wherein the endoscope shell is made of plastic, metal, or glass.

Embodiment 123. The method for capturing images using an endoscopic probe of any of embodiments 101 to 122, wherein a cross section of the endoscope shell is oval or round.

Embodiment 124. The method for capturing images using an endoscopic probe of any of embodiments 101 to 123, wherein the endoscope shell has a flattened optical window.

Embodiment 125. The method for capturing images using an endoscopic probe of any of embodiments 101 to 124, wherein the first mirror is fixed.

Embodiment 126. The method for capturing images using an endoscopic probe of any of embodiments 101 to 125, wherein the second mirror is fixed.

Embodiment 127. The method for capturing images using an endoscopic probe of any of embodiments 101 to 125, wherein the electromagnetic radiation is in the UV range.

It should be understood that the examples and embodiments described herein are for illustrative purposes only and that various modifications or changes in light thereof will be suggested to persons skilled in the art and are to be included within the spirit and purview of this application.

All patents, patent applications, provisional applications, and publications referred to or cited herein (including those in the "References" section) are incorporated by reference in their entirety, including all figures and tables, to the extent they are not inconsistent with the explicit teachings of this specification.

REFERENCES

[1] D. Huang, E. A. Swanson, C. P. Lin, J. S. Schuman, W. G. Stinson, W. Chang, M. R. Hee, T. Flotte, K. Gregory, and C. A. Puliafito, "Optical coherence tomography.," *Science*, vol. 254, no. 5035, pp. 1178-81, 1991.

[2] J. Sun, S. Guang, L. Wu, L. Liu, S. W. Choe, B. S. Sorg, and H. Xie, "3D in vivo optical coherence tomography based on a low-voltage, large-scan-range 2D MEMS mirror", *Opt. Express*, vol. 18, no. 12, pp. 12065-12075, 2010.

[3] X. Zhang, S. J. Koppal, R. Zhang, L. Zhou, E. Butler, and H. Xie, "Wide-angle structured light with a scanning MEMS mirror in liquid," *Opt. Express*, vol. 24, no. 4, p. 3479, 2016.

[4] K. Jia, S. Pal, and H. Xie, "An electrothermal tip-tilt-piston micromirror based on folded dual s-shaped bimorphs," *J. Microelectromechanical Syst.*, vol. 18, no. 5, pp. 1004-1015, 2009.

What is claimed is:

1. An endoscopic probe, comprising:
an endoscope shell;
a means for capturing electromagnetic radiation;
a first mirror disposed such that electromagnetic radiation entering through the endoscope shell is received at the first mirror and redirected to the means for capturing electromagnetic radiation; and
a liquid or a gel provided within the endoscope shell between the means for capturing electromagnetic radiation and the first mirror, and between the first mirror and the endoscope shell.

2. The endoscopic probe according to claim 1, wherein the first mirror is a microelectromechanical systems (MEMS) mirror.

3. The endoscopic probe according to claim 2, wherein the MEMS mirror is immersed in the liquid or gel.

4. The endoscopic probe according to claim 1,
wherein the first mirror is configured to tilt in at least one direction, wherein the first mirror is configured to be raised and lowered, and wherein the first mirror comprises at least one of the following: a first bimorph actuator for tilting the first mirror, raising the first mirror, or both; a piezo electric crystal for tilting the first mirror, raising the first mirror, or both; and second bimorph actuator that is an inverted-series-connected (ISC) Al/SlO$_2$ bimorph actuator for tilting the first mirror, raising the first mirror, or both.

5. The endoscopic probe according to claim 1, wherein the means for capturing electromagnetic radiation is a fiber or a camera.

6. The endoscopic probe according to claim 1, wherein the means for capturing electromagnetic radiation is a single mode fiber (SMF).

7. The endoscopic probe according to claim 1, further comprising a lens between the means for capturing electromagnetic radiation and the first mirror, wherein the liquid or the gel is provided between the first mirror and the lens and between the lens and the means for capturing electromagnetic radiation.

8. The endoscopic probe according to claim 7, wherein the lens is a gradient-index (GRIN) lens.

9. The endoscopic probe according to claim 1, further comprising a second mirror positioned to reflect electromagnetic radiation coming from the first mirror and to the means for capturing electromagnetic radiation, wherein the liquid or the gel is provided between the first mirror and the second mirror.

10. The endoscopic probe according to claim 1, wherein the electromagnetic radiation comprises visible light.

11. The endoscopic probe according to claim 1, wherein the electromagnetic radiation comprises infrared light.

12. The endoscopic probe according to claim 1, wherein the electromagnetic radiation comprises ultraviolet (UV) light.

13. The endoscopic probe according to claim 1, wherein a cross section of the endoscope shell is oval or circular.

14. The endoscopic probe according to claim 1, wherein the endoscope shell comprises a flattened optical window.

15. The endoscopic probe according to claim 1, further comprising a seal ring.

16. The endoscopic probe according to claim 1, further comprising a means for delivering electromagnetic radiation to the endoscopic probe, and wherein means for delivering electromagnetic radiation comprises at least one of the following: an optical fiber; a light-emitting diode (LED); and an electromagnetic radiation transmitting fiber.

17. The endoscopic probe according to claim 1, wherein the means for capturing electromagnetic radiation is immersed in the liquid or gel.

18. A method for capturing images using an endoscopic probe comprising an endoscope shell containing a liquid or a gel, the method comprising:

providing a means for capturing electromagnetic radiation within the endoscope shell;

receiving electromagnetic radiation through the endoscope shell at a first mirror;

redirecting the received electromagnetic radiation from the first mirror to the means for capturing electromagnetic radiation; and using Snell's window effect based on the liquid or the gel positioned between the first mirror and the endoscopic shell and between the means for capturing electromagnetic radiation and the endoscopic shell to expand a field of view captured by the means for capturing electromagnetic radiation.

19. The method according to claim 18 wherein the first mirror is a MEMS mirror.

20. The method according to claim 18, wherein the first mirror is configured to tilt in at least one direction, wherein the first mirror is configured to be raised and lowered, and wherein the first mirror comprises at least one of the following: a first bimorph actuator for tilting the first mirror, raising the first mirror, or both; a piezo electric crystal for tilting the first mirror, raising the first mirror, or both; and second bimorph actuator that is an inverted-series-connected (ISC) Al/SlO$_2$ bimorph actuator for tilting the first mirror, raising the first mirror, or both.

21. The method according to claim 18, wherein the means for capturing electromagnetic radiation is a fiber or a camera.

22. The method according to claim 18, wherein the means for capturing electromagnetic radiation is a single mode fiber (SMF).

23. The method according to claim 18, further comprising providing a lens between the means for capturing electromagnetic radiation and the mirror.

24. The method according to claim 23, wherein the lens is a GRIN lens.

25. The method according to claim 18, further comprising providing a second mirror positioned to reflect electromagnetic radiation coming from the first mirror and to the means for capturing electromagnetic radiation.

26. The method according to claim 18, wherein the electromagnetic radiation comprises visible light.

27. The method according to claim 18, wherein the electromagnetic radiation comprises infrared light.

28. The method according to claim 18, wherein a cross section of the endoscope shell is oval or circular.

29. The method according to claim 18, wherein the endoscope shell has a flattened optical window.

* * * * *